United States Patent [19]

Mita et al.

[11] Patent Number: 5,220,081
[45] Date of Patent: Jun. 15, 1993

[54] PROCESS FOR PREVENTING CONSOLIDATION OF P-DICHLOROBENZENE

[75] Inventors: Ryuichi Mita; Nobuo Shimuta; Deceased: By Shigeko Shimuta Executor; Omuta-Shi, Japan Mamoru Ueda; Shigeko Shimuta; Yosiro Nagatake; Toyohiro Tajiri, all of Omuta, Japan

[73] Assignee: Mitsui Toatsu Chemicals, Inc., Tokyo, Japan

[21] Appl. No.: 904,480

[22] Filed: Jun. 25, 1992

[30] Foreign Application Priority Data

Jun. 28, 1991 [JP] Japan .................. 3-158048

[51] Int. Cl.$^5$ .............................................. C07C 17/42
[52] U.S. Cl. ..................... 570/102; 570/101; 570/103
[58] Field of Search .............. 570/101, 190, 182, 102, 570/103, 264, 104

[56] References Cited

U.S. PATENT DOCUMENTS 4,777,305 10/1988 Cobb et al. .................. 570/206
5,001,290 3/1991 Hellman et al. ............. 570/206

FOREIGN PATENT DOCUMENTS 42-1006    1/1942  Japan .
42-10942   6/1942  Japan .
57-4615    1/1982  Japan .
58-11406   3/1983  Japan .
58-23851   5/1983  Japan .
58-134037  8/1983  Japan .
1-34207    7/1989  Japan .

Primary Examiner—Werren B. Lone
Attorney, Agent, or Firm—Burns, Doane, Swecker & Mathis

[57] ABSTRACT

A triethylene glycol derivative is added to p-dichlorobenzene so as to prevent consolidation and improve flowability of p-dichlorobenzene.

3 Claims, No Drawings

PROCESS FOR PREVENTING CONSOLIDATION OF P-DICHLOROBENZENE

BACKGROUND OF THE INVENTION

Field of the Invention

The invention relates to a process for preventing consolidation and improving flowability of p-dichlorobenzene, and more particularly, to a process for preventing consolidation and improving flowability of p-dichlorobenzene by adding a certain compound thereto.

Description of Related Art p-Dichlorobenzene (hereinafter referred to as PDCB) is usually formed into tablets, balls or rods and is widely used as mothballs or deodorant for clothing. It is also a useful compound as a raw material for producing some high polymer compounds.

PDCB is usually produced by chlorinating benzene, separating p-dichlorobenzene from the chlorination products containing chlorobenzene, o-dichlorobenzene, p-dichlorobenzene and others and purifying the p-dichlorobenzene. Further, the p-dichlorobenzene is taken out in the form of flakes, and is directly or after the flakes are formed into particles, shipped to makers for shaping and processing the particles or flakes.

The melting point of PDCB is low though it depends on the impurity content, and even the melting point of the pure compound is as low as 53° C. Therefore, PDCB products shipped in the form of flakes are very liable to consolidate during storing and transportation.

When PDCB is shaped and processed, for example, ground and tableted, the flowability and the like are poor and therefore, the processibility is markedly lowered.

In order to solve such a problem of consolidation of PDCB, various methods have been tried. As a representative method, it is known to add an additive to prevent the consolidation.

For example, Japanese Patent Publication Nos. 10942/1967 and 1006/1967 disclose a method of adding a surface active agent. Japanese Patent Application Laid-open No. 134037/1983 and Japanese Patent Publication No. 34207/1989 disclose a method of adding a volatile silicone oil.

However, these methods are not always satisfactory, partly because the vapor pressures of the additives themselves are very low or almost zero so that the additives remain after PDCB has sublimed and are liable to stain the cloth, and partly because the actual effect of the additive is not sufficient.

As additives for preventing consolidation of PDCB, Japanese Patent Publication No. 4615/1982 discloses benzyl alcohol, Japanese Patent Publication No. 23851/1983 diethylene glycol derivatives, and Japanese Patent Publication No. 11406/1983 both benzyl alcohol and diethylene glycol derivatives at a certain ratio.

Among these proposed methods, a method of adding only benzyl alcohol does not sufficiently prevent the consolidation, and a method of adding only diethylene glycol derivatives can markedly prevent the consolidation, but the resulting shaped articles such as tablets are fragile as described in Japanese Patent Publication No. 11406/1983 and therefore, said derivatives alone can not be used as additives.

For the purpose of retaining the hardness of the shaped articles and further preventing the consolidation, both a diethylene glycol derivative and benzyl alcohol should be used in combination. Such a method as above is not always preferable since two types of additives must be used.

SUMMARY OF THE INVENTION

An object of the present invention is to provide a process for preventing consolidation of PDCB.

Another object of the present invention is to provide a process for improving flowability of PDCB after grinding.

A further object of the present invention is to provide a process for retaining a sufficient hardness of shaped articles of PDCB together with attaining at least one object as mentioned above.

Still another object of the present invention is to provide a process for preventing consolidation of PDCB with nothing remaining after PDCB has been sublimed.

A still further object of the present invention is to provide PDCB having at least one of the improved effects over an extended time.

According to the present invention, there is provided a process for preventing consolidation and improving flowability of p-dichlorobenzene which comprises adding to p-dichlorobenzene a triethylene glycol derivative of the formula (1), $$R^1OCH_2CH_2OCH_2CH_2OCH_2CH_2OR^2 \qquad (1)$$

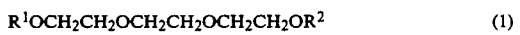

where $R^1$ and $R^2$ are independently selected from the group consisting of hydrogen atom, aliphatic alkyl group having 1-10 carbon atoms and aliphatic alkyl carbonyl group having 1-10 carbon atoms.

DESCRIPTION OF THE PREFERRED EMBODIMENTS

Exemplary suitable triethylene glycol derivatives are:
triethylene glycol,
triethylene glycol monomethyl ether,
triethylene glycol monoethyl ether,
triethylene glycol monopropyl ether,
triethylene glycol monobutyl ether,
triethylene glycol monopentyl ether,
triethylene glycol monohexyl ether,
triethylene glycol monoheptyl ether,
triethylene glycol monooctyl ether
triethylene glycol mononyl ether,
triethylene glycol monodecyl ether,
triethylene glycol dimethyl ether,
triethylene glycol diethyl ether,
triethylene glycol dipropyl ether
triethylene glycol dipentyl ether,
triethylene glycol dihexyl ether,
triethylene glycol diheptyl ether,
triethylene glycol dioctyl ether,
triethylene glycol dinonyl ether,
triethylene glycol didecyl ether
triethylene glycol monoacetate,
triethylene glycol monopropionate,
triethylene glycol monobutyrate,
triethylene glycol monopentanoate,
triethylene glycol monohexanoate,
triethylene glycol monoheptanoate,
triethylene glycol monooctanoate,
triethylene glycol monononanoate,
triethylene glycol monodecanoate,
triethylene glycol diacetate, triethylene glycol dipropionate,
triethylene glycol dibutyrate,
triethylene glycol dipentanoate,
triethylene glycol dihexanoate,
triethylene glycol diheptanoate,
triethylene glycol dioctanoate,
triethylene glycol dinonanoate,
triethylene glycol didecanoate, and the like.

Among these compounds, triethylene glycol or triethylene glycol diacetate exhibits a very excellent effect. These additives are usually used alone, but may be naturally used in combination.

When the amount of the additive is too little, the effect is lowered. On the contrary, when the amount is too much, the additive undesirably exudes from the product.

Therefore, the amount of the additive is usually used in an amount of 0.005–0.5% by weight, preferably in an amount of 0.01–0.3% by weight based on the weight of PDCB.

When the additive is used in an amount of the above-mentioned range, various characteristics such as anticonsolidation and the like of PDCB can be improved to a great extent, and further the hardness of the shaped articles such as tablets and the like can be sufficiently retained.

In addition, these additives neither remain after PDCB has sublimed, nor stain cloth, and therefore, the additives are very excellent.

According to the present invention, PDCB may be treated with the additive, for example, by adding the additive to a molten PDCB in a prescribed amount before taking the PDCB in the form of flakes and crystallizing the PDCB as flake-like crystals by means of a flaker or the like, or by spraying a prescribed amount of the additive on the PDCB product not containing an additive.

Or, when PDCB product is taken out by means of recrystallization, the additive may be added to a solvent for recrystallization and then the solution is cooled to separate the PDCB.

In the case of diethylene glycol derivatives in the prior art, for example, when 0.1% of diethylene glycol dibutyl ether is added to PDCB, the consolidation force of the resulting PDCB is 1/5 times that of PDCB not containing the additive, but the hardness of the shaped article (e.g. tablets) is also decreased to 1/5. The hardness of tablets can be retained at the substantially same level as that of PDCB not containing an additive by combining the diethylene glycol derivative with benzyl alcohol as disclosed in Japanese Patent Publication No. 11406/1983.

On the contrary, when, for example, triethylene glycol diacetate is added in an amount of 0.1% based on PDCB, the consolidation force is decreased to 1/5 times that of PDCB not containing an additive or less, and further, when formed into tablets, the hardness of PDCB is not so lowered and is substantially the same as that of PDCB article containing no additive.

According to the present invention, consolidation of PDCB can be prevented and flowability of PDCB after grinding can be improved by the particular triethylene glycol derivative as an additive.

Such desirable effects are durable for a long period of time, and even when only a small account of the additive is used, the effects are durable.

In addition, shaped articles of PDCB retains a sufficient hardness. After sublimation of PDCB, nothing remains, that is, the additive does not stain, for example, cloth.

In the following, the present invention is explained referring to examples. In the examples, various tests are as shown below.

1. Preparation of flake product

PDCB was melted at 60° C., and a prescribed amount of the additive was dissolved therein and then gradually poured into a stainless steel vat cooled to 10° C. in advance. After crystallization, the PDCB was peeled off and formed into flakes.

2. Consolidation force

Two cylinders made of a resinous material, each having an inner diameter of 5 cm were prepared. One cylinder (lower cylinder) placed vertically on a flat plate such that one end of the cylinder closely contacts the flat surface.

The other cylinder (upper cylinder) was put on the lower cylinder such that the upper end portion of the lower cylinder consists with the lower end portion of the upper cylinder.

The inner hollow portion thus formed by the combined two cylinders was filled with ground PDCB having a particle size of 12–20 mesh prepared by grinding PDCB with an automatic mortar followed by screening. Then a load of 1 kg was applied from the top and after the PDCB was allowed to stand for 15 hours, the load was removed.

The lower cylinder is fixed to the flat surface, and the upper cylinder was pulled horizontally and the force required for beginning of movement was defined as the consolidation force.

3. Grinding test

In an automatic mortar was placed 100 g of PDCB flakes and ground for 5 min., and then the ground particles was discharged by inclining the mortar.

The manner in which the particles were discharged was designated as shown below:

⊙: The total amount of the particles was easily discharged only by inclining the mortar.

○: About 80% of the amount of the particles was easily discharged, but about 20% or less remained in the mortar, but the remaining amount was wholly discharged by tapping the mortar.

△: About 50% of the amount of the particles was discharged only by inclining the mortar.

X: Only 20% or less of the amount of the particle was discharged by inclining the mortar and a large amount of the particles remained attached to the mortar.

4. Tablet hardness

Various types of PDCB were ground and shaped into tablets of a drum type of 20 mm in diameter and about 9 mm in the central thickness by a molding machine (tableting machine). Then the tablets thus shaped were placed horizontally on a metal plate and a metal ball of 13 g in weight was dropped from various heights through a resin pipe by free falling, and the degree of cracking was examined. The evaluation was as shown below.

○: No crack was formed though the portion hit by the falling metal ball was depressed somewhat.

△: Crack was formed at the upper surface of a tablet, but did not reach the back surface of the tablet.

X: Crack reached the back surface.

XX: A tablet was completely split.

With respect to the hardness of tablet, a hardness testing machine was separately used to measure the actual hardness.

EXAMPLES 1-13 and COMPARATIVE EXAMPLE 1

Various triethylene glycol derivatives were added to PDCB in an amount of 0.1% based on the weight of PDCB to prepare flake products of PDCB.

The results of consolidation force test and grinding test are shown in Table 1.

TABLE 1

| | Additive | Consolidation force (g) | Grinding test |
|---|---|---|---|
| Example 1 | Triethylene glycol | 225 | ⊙ |
| Example 2 | Triethylene glycol diethyl ether | 290 | ○ |
| Example 3 | Triethylene glycol di-n-butyl ether | 275 | ○ |
| Example 4 | Triethylene glycol di-n-decyl ether | 260 | ○ |
| Example 5 | Triethylene glycol mono-ethyl ether | 230 | ○ |
| Example 6 | Triethylene glycol mono-n-butyl ether | 235 | ○ |
| Example 7 | Triethylene glycol mono-n-hexyl ether | 255 | ○ |
| Example 8 | Triethylene glycol mono-acetate | 240 | ○ |
| Example 9 | Triethylene glycol mono-n-propionate | 255 | ○ |
| Example 10 | Triethylene glycol mono-n-butyl ether acetate | 230 | ○ |
| Example 11 | Triethylene glycol mono-n-ethyl ether acetate | 245 | ○ |
| Example 12 | Triethylene glycol diacetate | 210 | ⊙ |
| Example 13 | Triethylene glycol di-propionate | 290 | ○ |
| Comparative Example 1 | Not added | 1,070 | x |

EXAMPLES 14-19 and COMPARATIVE EXAMPLES 2-3

The amounts of triethylene glycol or triethylene glycol diacetate added were changed to prepare PDCB flake products. Table 2 shows the test results of the flake products as to various characteristics.

In addition, for comparison, PDCB flake product containing no additive and PDCB flake product containing diethylene glycol monobutyl ether acetate disclosed in Japanese Patent Publication No. 23851/1983 were also tested.

TABLE 2

| | Additive | | Consolidation force(g) | Grinding test | Tablet strength | |
|---|---|---|---|---|---|---|
| | Compound | Amount (%/PDCB) | | | Falling test(40 cm) | Hardness (kg) |
| Example 14 | Triethylene glycol | 0.05 | 255 | ⊙ | ○ | 2.05 |
| Example 15 | Triethylene glycol | 0.1 | 225 | ⊙ | ○ | 2.00 |
| Example 16 | Triethylene glycol | 0.3 | 200 | ⊙ | Δ | 1.95 |
| Example 17 | Triethylene glycol diacetate | 0.05 | 245 | ⊙ | ○ | 2.20 |
| Example 18 | Triethylene glycol diacetate | 0.1 | 210 | ⊙ | ○ | 2.15 |
| Example 19 | Triethylene glycol diacetate | 0.3 | 190 | ⊙ | Δ | 2.00 |
| Comparative Example 2 | Not added | — | 1,070 | x | ○ | 2.35 |
| Comparative Example 3 | Diethylene glycol monobutyl ether acetate | 0.1 | 265 | ⊙ | x | 1.70 |

EXAMPLE 20, COMPARATIVE EXAMPLE 4-5

Triethylene glycol diacetate was added to PDCB in an amount of 0.1% by weight based on PDCB to prepare a PDCB flake product.

In a similar manner to that described above, diethylene glycol monobutyl ether acetate disclosed in Japanese Patent Publication No. 23851/1983 was added to PDCB in the same amount (% by weight) as above to prepare a PDCB flake product.

In a similar manner to that described above, diethylene glycol monobutyl ether acetate and benzyl alcohol disclosed in Japanese Patent Publication No. 11406/1983 were added to PDCB in the same amount (% by weight) as above to prepare a PDCB flake product.

The each flake product containing an additive was ground with a mortar and screened to form the particles of 12-20 mesh.

The change of consolidation force with time of the products thus ground and screened was investigated according to the method of measuring consolidation force by changing the period of time during which a load was applied thereto.

The result is shown in Table 3.

TABLE 3

| | PDCB | | Change with time of consolidation force (g) | | |
|---|---|---|---|---|---|
| | Additive | Amount %/PDCB | 16 hours | 2 days | 7 days |
| Example 20 | Triethylene glycol diacetate | 0.1 | 220 | 490 | 1,010 |
| Comparative Example 4 | Diethylene glycol monobutyl ether acetate | 0.1 | 350 | 1,280 | 2,000 |
| Comparative Example 5 | Diethylene glycol monobutyl ether | 0.1 | 550 | 1,640 | 2,130 |

| | PDCB | | Change with time of consolidation force (g) | | |
|---|---|---|---|---|---|
| Additive | | Amount %/PDCB | 16 hours | 2 days | 7 days |
| (a) | acetate + Benzyl alcohol | | | | |

Note: (a) Two types of additives were added to PDCB in an amount of 0.05% each and in a total amount of 0.1% based on PCBD.

What is claimed is:

1. A process for preventing consolidation and improving flowability of p-dichlorobenzene which comprises adding to p-dichlorobenzene a triethylene glycol derivative of the formula (1), $$R^1OCH_2CH_2OCH_2CH_2OCH_2CH_2OR^2 \quad (1)$$

where $R^1$ and $R^2$ are independently selected from the group consisting of hydrogen atom, aliphatic alkyl group having 1-10 carbon atoms and aliphatic alkyl carbonyl group having 1-10 carbon atoms.

2. The process according to claim 1 in which the triethylene glycol derivative is triethylene glycol or triethylene glycol diacetate.

3. The process according to claim 1 in which the triethylene glycol derivative is added in an amount of 0.005-0.5% by weight based on the weight of p-dichlorobenzene.

* * * * *

UNITED STATES PATENT AND TRADEMARK OFFICE
CERTIFICATE OF CORRECTION

PATENT NO. :  5,220,081
DATED      :  June 15, 1993
INVENTOR(S) : Mita et al

It is certified that error appears in the above-identified patent and that said Letters Patent is hereby corrected as shown below:

On the title page, inventors item: [75], after "Mamoru Ueda;" delete "Shigeko Shimuta;".

Signed and Sealed this

Fifth Day of April, 1994

Attest:

*Attesting Officer*

BRUCE LEHMAN

*Commissioner of Patents and Trademarks*